US010215686B2

(12) United States Patent
Hombo et al.

(10) Patent No.: US 10,215,686 B2
(45) Date of Patent: Feb. 26, 2019

(54) METAL CORROSION RESISTANCE EVALUATION METHOD AND EVALUATION DEVICE USING IN-LIQUID POTENTIAL MEASUREMENT

(71) Applicant: Hitachi, Ltd., Chiyoda-ku, Tokyo (JP)

(72) Inventors: Kyoko Hombo, Tokyo (JP); Kenya Ohashi, Tokyo (JP); Masahiro Itoh, Tokyo (JP); Mitsuharu Ikeda, Tokyo (JP); Takeshi Fukuma, Kanazawa (JP); Naritaka Kobayashi, Kanazawa (JP); Shoichiro Ogata, Kanazawa (JP)

(73) Assignee: Hitachi, Ltd., Tokyo (JP)

( * ) Notice: Subject to any disclaimer, the term of this patent is extended or adjusted under 35 U.S.C. 154(b) by 515 days.

(21) Appl. No.: 14/905,048

(22) PCT Filed: Jul. 22, 2013

(86) PCT No.: PCT/JP2013/069728
§ 371 (c)(1),
(2) Date: Jan. 14, 2016

(87) PCT Pub. No.: WO2015/011743
PCT Pub. Date: Jan. 29, 2015

(65) Prior Publication Data
US 2016/0146719 A1 May 26, 2016

(51) Int. Cl.
*G01N 17/00* (2006.01)
*G01Q 30/14* (2010.01)
(Continued)

(52) U.S. Cl.
CPC ........... *G01N 17/006* (2013.01); *G01N 17/02* (2013.01); *G01Q 30/14* (2013.01); *G01Q 60/30* (2013.01)

(58) Field of Classification Search
CPC ...... G01N 17/006; G01N 17/02; G01Q 30/14; G01Q 60/30
(Continued)

(56) References Cited

U.S. PATENT DOCUMENTS 6,053,035 A * 4/2000 Nomura .............. G01N 27/305
205/777.5
2014/0223614 A1 8/2014 Fukuma et al.
2015/0115770 A1* 4/2015 Johnson .............. B81B 3/0086
310/309

FOREIGN PATENT DOCUMENTS

JP 2000-146823 A 5/2000
JP 2007-263788 A 10/2007
(Continued)

OTHER PUBLICATIONS

Extended European Search Report issued in counterpart European Application No. 13890197.0 dated Mar. 1, 2017 (10 pages).
(Continued)

*Primary Examiner* — Melissa Koval
*Assistant Examiner* — Trung Nguyen
(74) *Attorney, Agent, or Firm* — Crowell & Moring LLP (57) ABSTRACT

The objective of the present invention is to provide a corrosion resistance evaluation method and evaluation device that make it possible to estimate crevice corrosion depth and pitting depth in a short period of time. A corrosion resistance evaluation method according to the present invention is characterized in that the surface potential of a metal under evaluation is measured in a state in which the metal is immersed in a usage-environment liquid, the surface potential distribution of the metal is determined, the surface potential differences in the microstructure of the metal are calculated on the basis of the surface potential distribution, and the corrosion rate of crevice corrosion and corrosion rate of pitting are predicted using the maximum surface potential difference from among the calculated surface potential differences as an evaluation index for corrosion evaluation.

14 Claims, 7 Drawing Sheets

(51) Int. Cl.
 *G01Q 60/30* (2010.01)
 *G01N 17/02* (2006.01)
(58) Field of Classification Search
 USPC ........ 324/694–711, 200, 233, 500, 521, 622, 324/683, 525, 549, 69; 702/7, 9, 11
 See application file for complete search history.

(56) References Cited

FOREIGN PATENT DOCUMENTS

| | | |
|---|---|---|
| JP | 2009-180556 A | 8/2009 |
| WO | WO 2013/038659 A1 | 3/2013 |

OTHER PUBLICATIONS

Souto et al., "Uses of Scanning Electrochemical Microscopy in Corrosion Research", Microscopy: Science, Technology, Applications and Education, vol. 3, No. 4, Jan. 1, 2010, pp. 1769-1780, FORMATEX, XP055342976.
Japanese- language Office Action issued in counterpart Japanese Application No. 2015-528014 dated Nov. 29, 2016 with English translation (5 pages).
Pan, "Corrosion Behavior of a Duplex Stainless Steel Under Cyclic Loading: a Scanning Kelvin Probe Force Microscopy (SKPFM) Based Microscopic Study", Journal of Applied Electrochemistry, Dec. 2012, vol. 42, No. 12, pp. 1049-1056.
International Search Report (PCT/ISA/210) issued in PCT Application No. PCT/JP2013/069728 dated Sep. 17, 2013, with English translation (four (4) pages).
Keisuke Funatsu et al., "Influence of Surface Potential Difference at Microscopic Interface on Initial Galvanic Corrosion Phenomena of Magnesium Alloy", Transactions of the Japan Society of Mechanical Engineers, Series A, Oct. 25, 2012, pp. 1432-1445, with English Abstract.
Yasuyuki Katada et al., "Microscopic Study on Corrosion Properties of Nitrogen-Bearing Stainless Steel", Ultra-Steel Workshop, Jan. 13, 2000, (three (3) pages).

* cited by examiner

METAL CORROSION RESISTANCE EVALUATION METHOD AND EVALUATION DEVICE USING IN-LIQUID POTENTIAL MEASUREMENT

TECHNICAL FIELD

The present invention relates to a metal corrosion resistance evaluation method and an evaluation device using in-liquid potential measurement.

BACKGROUND ART

Metal corrosion is a phenomenon where metal elutes or a corrosion product is precipitated due to chemical reaction (oxidation-reduction reaction) that occurs between metal and water interface. Metal is widely used not only in familiar products such as household appliances, but also in machine parts and building structures. Metal corrosion causes deterioration in function and performance of such artificial products, and is one of major problems that prevent long-term stable use. Thus, researches related to the occurrence mechanism of corrosion and the development of effective anticorrosion techniques have been conducted for a long time.

Actual metal corrosion phenomena progress over the years, i.e., over several years to several tens of years. It has been therefore difficult to find corrosion pitting in a short period of time. Thus, there has been employed a test method of measuring a crevice corrosion depth and a pitting depth by immersing a metal in the same corrosive liquid as that under the usage environment such as seawater for one year or more. Under the circumstances, a prediction technique of a metal corrosion rate that enables the prediction of a corrosion progress level in a short period of time has been demanded.

As a prediction technique of metal corrosion/anticorrosion problems, PTL 1 discloses a method of using polarization curve data. Since an actual polarization curve changes with time, PTL 1 discloses a method of measuring an actual surface potential or current density, and obtaining a polarization curve using the measured value to estimate a polarization curve obtainable after the lapse of a certain period of time.

In addition, PTL 2 discloses a device for evaluating the potential of a sacrificial anticorrosion metal. The device includes a means for cooling and heating a corrosive liquid and a means for spraying the corrosive liquid onto a test piece. The device further includes a means for adjusting a crevice portion and a means for measuring the potential of the test piece via a standard electrode.

In addition, PTL 3 discloses a method of measuring the surface potential and the weight change of a metal to obtain the correlation existing between the surface potential and the corrosion amount of the metal, and quantitatively evaluating a corrosion amount from the measured surface potential on the basis of the obtained correlation.

CITATION LIST

Patent Literatures

PTL 1: JP 2007-263788 A
PTL 2: JP 2009-180556 A
PTL 3: JP 2000-146823 A

SUMMARY OF INVENTION

Technical Problem

Conventional prediction techniques of corrosion/anticorrosion problems as proposed in PTLs 1 to 3 are based on macro electrochemical measurement. That is, the measurement of the potential and the current density is macro measurement, and such techniques are not suitable for locally measuring the microstructure of a metal. Thus, local corrosion, i.e., specific phenomena such as corrosion pits and pitting cannot be detected by the conventional techniques. Accordingly, there has been an unpredictable corrosion mode, making it difficult to estimate the lifetime.

As an example, duplex phase stainless steel is composed of two phases different in chemical composition (content of Cr, Mo, or N), such as an $\alpha$ phase (ferrite phase) and a $\gamma$ phase (austenite phase). Corrosion resistance is often discussed on the basis of macro chemical compositions and the area ratio between two phases. Nevertheless, in actual cases, the phases precipitated through a manufacturing process are not limited to two phases, and a plurality of precipitates may exist. In addition, even if macro chemical compositions are the same, the chemical compositions of micro phases may be different in some cases. It has been therefore difficult to predict the depth of micro corrosion such as pitting and crevice corrosion, i.e., local corrosion by an electrochemical method as seen in the above-described patent literatures.

The objective of the present invention is to provide a corrosion resistance evaluation method and an evaluation device that make it possible to estimate a crevice corrosion depth and a pitting depth in a short period of time.

Solution to Problem

The subject application includes a plurality of means for solving the above issues. As an example of these means, for example, a metal corrosion resistance evaluation method of the present invention includes measuring a surface potential of a metal under evaluation in a state in which the metal is immersed in a usage-environment liquid to determine a surface potential distribution of the metal, calculating surface potential differences in a microstructure of the metal on the basis of the surface potential distribution, and predicting a corrosion rate of crevice corrosion or a corrosion rate of a pitting of the metal using a maximum surface potential difference from among the calculated surface potential differences as an evaluation index for corrosion evaluation.

Advantageous Effects of Invention

According to the present invention, a corrosion resistance evaluation method and an evaluation device that make it possible to estimate a crevice corrosion depth and a pitting depth in a short period of time are provided.

DESCRIPTION OF EMBODIMENTS

Corrosion is attributed to electrochemical reaction in which oxidation is caused (an electron is lost) at an anode and reduction is caused (an electron is received) at a cathode. Thus, conventional techniques evaluate corrosion properties and corrosion behavior by measuring an anode/cathode polarization curve by measuring the corrosion potential of a sample using a potentiostat or by flowing current and measuring the potential using a galvanostat. Nevertheless, the potential values measured by these methods are average values of all samples. Thus, such techniques cannot measure a local potential distribution. In particular, as for local corrosion such as the ones called pitting and stress corrosion crack, it is necessary to identify at which location the corrosion progresses, and how much potential the corrosion shows when the corrosion progresses. In the conventional electrochemical measurement, the macro potential, i.e., the mixed potential of different phases is merely measured instead of measuring the respective potentials of metal structures. It is therefore difficult to predict such local corrosion.

Originally, corrosion is closely related to the potential in a corrosive liquid of a metal structure. Galvanic corrosion serves as a typical example of such corrosion. A joint part of different metal compositions has different potentials, and such a potential difference functions as drive force to progress corrosion. In other words, as the potential difference increases, corrosion current flows to cause dissolution reaction of a metal, so that pitting and crevice corrosion occur. If the in-surface potentials of a microstructure can be measured, corrosiveness is expected to be identified on the basis of the potential difference in the microstructure. In this regard, the present inventors have found out, as a result of keen examination, that a local potential distribution in which local corrosion occurs can be measured using an open-loop electric potential microscopy (hereinafter, referred to as "OL-EPM") to which a part of functions of an atomic force microscope (AFM) is applied. The present inventors have further found out that there is a correlation between the corrosion rates of the crevice corrosion and the pitting and the in-surface potential difference in the microstructure, and the surface potential difference serves as an evaluation index for corrosion evaluation. The present inventors have thereby reached the invention.

The present invention is a metal corrosion resistance evaluation method of measuring the surface potential of a metal under evaluation in a state in which the metal is immersed in a usage environment liquid to determine the surface potential distribution of the metal, calculating the surface potential differences in the microstructure of the metal on the basis of the surface potential distribution, and predicting the corrosion rate of the crevice corrosion or the corrosion rate of the pitting of the metal using the maximum surface potential difference from among the calculated surface potential differences as an evaluation index for corrosion evaluation.

In the present invention, the surface potential difference in the microstructure means the surface potential difference in crystal grains at the grain boundary and in the grains, the surface potential difference in grains with different plain directions in crystal grains, the surface potential difference between a precipitate and a mother phase, the surface potential difference between a precipitate and a segregation layer, the surface potential difference between a segregation layer and a mother phase, the surface potential difference between two phases, the surface potential difference between a precipitated phase and a mother phase, the surface potential difference between a precipitated phase and a segregation layer, or the surface potential difference between a precipitated phase and a precipitate. As for the galvanic corrosion, the above-described surface potential difference in crystal grains being microstructures at the grain boundary and in the grains, and the surface potential difference in grains with different plain directions in crystal grains function as drive force to progress the corrosion. The larger the potential difference is, the more the corrosion easily progresses. As the actual evaluation result using duplex phase stainless steel, the relation between the corrosion rates of the crevice corrosion and the pitting and the in-surface potential difference in the microstructure exhibited such a tendency that the larger the surface potential difference is, the higher the corrosion rates of the crevice corrosion and the pitting are. Thus, in the present invention, from among the calculated surface potential differences in the microstructure of the metal, the maximum surface potential difference is used as an evaluation index for corrosion evaluation.

In the present invention, a usage-environment liquid refers to a liquid solution to which a metal under evaluation is exposed under the environment where the metal is used. Examples of such a liquid include seawater and chemicals. Note that it is important to measure the surface potential difference using the same liquid solution as a liquid solution to which the metal is actually exposed under the usage environment, because the surface potential of the microstructure varies depending on the types of liquid solutions.

The corrosion rate of the crevice corrosion or the corrosion rate of the pitting of a metal can be predicted on the basis of the surface potential difference in the following manner. First, using two or more metals with different compositions, of which the corrosion rates of the crevice corrosion or the corrosion rates of the pitting in a usage environment are known, the maximum surface potential difference in the liquid is determined in advance using the same method as the above-described method. The correlation between the determined surface potential difference and the corrosion rate is stored in advance as measurement data. Then, a corrosion rate is predicted on the basis of the surface potential difference in the microstructure that has been measured for a metal under evaluation of which the corrosion rate is unknown, and the above-described measurement data. If there is no data on the corrosion rate of the crevice corrosion or the corrosion rate of the pitting of the metal in a specific liquid solution, the corrosion rate of the crevice corrosion or the corrosion rate of the pitting is measured for two or more metals with different compositions, using a method with high exactitude such as a long-term immersion test, and the correlation between the surface potential difference and the corrosion rate is determined in advance using the same method as the above-described method. In this case, a long-term test is required similarly to the conventional techniques. Nevertheless, if the correlation is once determined, a long-term test is no longer required for other metal materials with different compositions, of which the corrosion rates are unknown. This consequently brings about such an effect that the corrosion rate can be evaluated in a short period of time.

An evaluation device for executing an evaluation method according to the present invention is characterized in that the evaluation device includes a potential measurement device for measuring the surface potentials of a sample in a liquid, and including a probe, an alternating-current source for applying a bias voltage between the probe and a metal serving as the sample, a capacitor provided in a closed circuit for applying a bias voltage between the probe and the sample, a displacement measurement unit for outputting a voltage signal associated with interacting force exerted between the probe and the sample, and a signal detector for detecting an electrostatic force signal having a specific frequency component contained in the voltage signal output by the displacement measurement unit to output a value corresponding to the detected signal, a database storing the relation between the surface potential difference in the microstructure of a metal with various compositions in a specific liquid, and the corrosion rate of the crevice corrosion or the pitting, and a prediction means for calculating the surface potential difference in the microstructure of the metal from the surface potentials measured by the potential measurement device and for predicting the corrosion rate at which the crevice corrosion or the pitting of the metal occurs, on the basis of the surface potential difference in the microstructure of the metal, by referring to data in the database.

An embodiment according to a metal corrosion resistance evaluation method and an evaluation device of the present invention will be described below.

Figure 1:
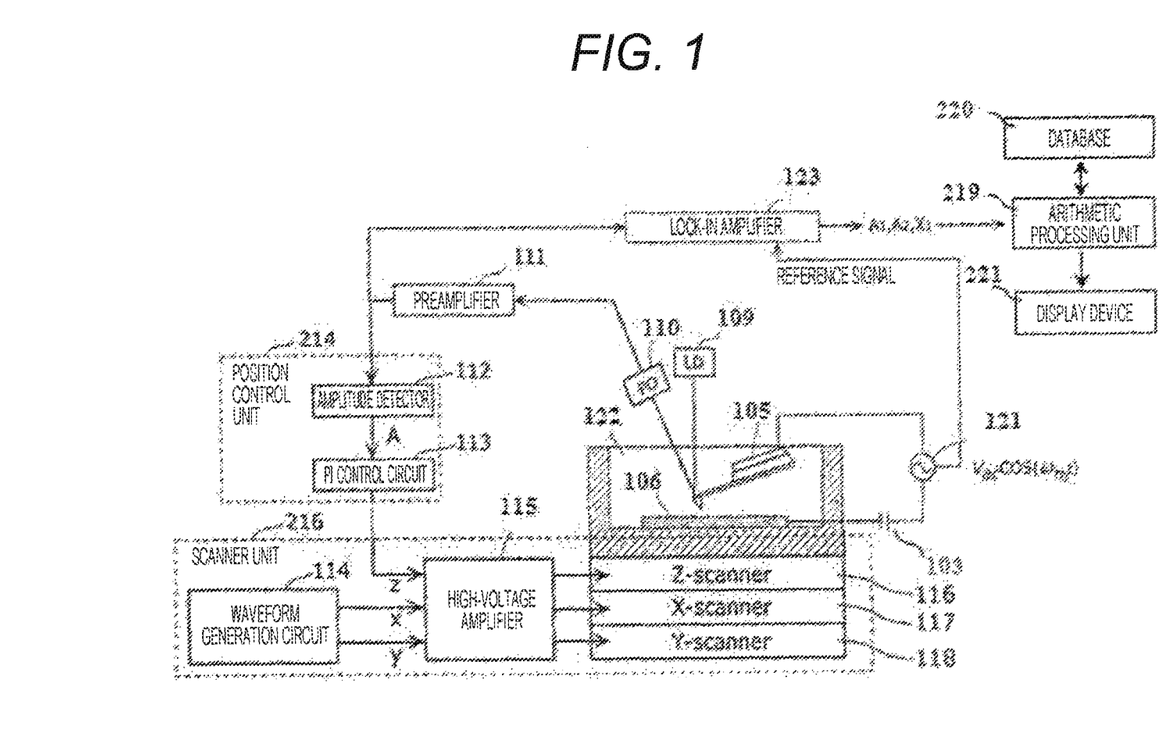
FIG. 1 is a configuration diagram illustrating an overview of an evaluation device using an open-loop electric potential microscopy (OL-EPM) used in the present invention.

The description will be given of an example of a corrosion resistance evaluation device using an OL-EPM, which serves as a potential measurement device for measuring the surface potential and the surface potential distribution of a metal surface in a liquid. FIG. 1 illustrates a configuration diagram of a corrosion resistance evaluation device using an OL-EPM serving as a potential measurement device. The OL-EPM measures the surface potential of a metal serving as a sample 106 that is placed in a liquid solution 122. The OL-EPM includes a cantilever 105, an alternating-current source 121, a laser diode (LD) 109, a photodiode (PD) 110, a preamplifier 111, a lock-in amplifier 123, and a capacitor 103.

The alternating-current source 121 applies an alternating-current (AC) bias voltage between the sample 106 and a probe electrode provided at the leading end of the cantilever 105. On the basis of the AC bias voltage, an electric field is generated between the probe electrode and the sample 106. In the OL-EPM, a modulating frequency $\omega_m$ of an AC bias voltage is 10 kHz or more.

At this time, by electrostatic force $F_{es}$ generated between the probe electrode and the sample 106, the leading end of the cantilever 105 displaces in a vertical direction. An OL-EPM 100 measures the displacement using the LD 109 and the PD 110. Specifically, the PD 110 for position detection receives the reflected light of a semiconductor laser beam emitted from the LD 109 onto the leading end of the cantilever 105. In accordance with the displacement in a z-axis direction of the leading end portion of the cantilever 105, a light reception position of the PD 110 changes. The OL-EPM extracts this change via the preamplifier 111 as a voltage change amount. Furthermore, the lock-in amplifier 123 serving as a signal detector detects a specific frequency component contained in the voltage change amount, whereby the OL-EPM obtains the surface potential of the sample 106.

The capacitor 103 prevents a direct-current offset voltage from getting in. The direct-current offset voltage can be unexpectedly generated during the application of an AC bias voltage. This can prevent the occurrence of unnecessary electrochemical reaction. More specifically, the electrostatic force $F_{ea}$ in the OL-EPM can be obtained by the following formula, using $V_{ts}=V_s-V_{ac}\cos(\omega_m t)$:

[Mathematical Formula 1]

$$F_{es} = \frac{1}{2}\frac{\partial C_{ts}}{\partial z}\left[V_s^2 + \frac{1}{2}V_{ac}^2 - 2V_s V_{ac}\cos(\omega_m t) + \frac{1}{2}V_{ac}^2\cos^2(2\omega_m t)\right]. \quad \text{(Formula 1)}$$

In the formula, the respective magnitudes of $\omega_m$ and $2\omega_m$ components contained in the electrostatic force $F_{es}$ are represented by $A_1$ and $A_2$. Using a transfer function $G(\omega)$ of the cantilever 105, $A_1$ and $A_2$ can be obtained by the following Mathematical Formulae (2) and (3):

[Mathematical Formula 2]

$$A_1 = G(\omega_m)\left|\frac{\partial C_{ts}}{\partial z}V_s V_{ac}\right|, \text{ and} \quad \text{(Formula 2)}$$

[Mathematical Formula 3]

$$A_2 = G(2\omega_m)\left|\frac{1}{4}\frac{\partial C_{ts}}{\partial z}V_{ac}^2\right|. \quad \text{(Formula 3)}$$

In addition, the transfer function $G(\omega)$ of the cantilever 105 can be obtained by the following Mathematical Formula (4):

[Mathematical Formula 4]

$$G(\omega) = \frac{1}{k}\frac{1}{\sqrt{[1-(\omega/\omega_0)^2]^2 + (\omega/\omega_0 Q)^2}}. \quad \text{(Formula 4)}$$

In the formula, k, $\omega_0$ ($=2\pi f_0$), and Q respectively represent a spring constant, a resonance frequency, and a Q value of the cantilever 105.

In addition, $A_1$ and $A_2$ can be measured by the lock-in amplifier 123. $G(\omega_m)$ and $G(2\omega_m)$ can be calculated by Mathematical Formula (4) if k, $\omega_0$, and Q are identified. These parameters can be obtained by measuring the thermal vibration spectrum ($n_z$) of the cantilever 105, and fitting the measured thermal vibration spectrum ($n_z$) using the following Mathematical Formula (5):

[Mathematical Formula 5]

$$n_z = \sqrt{\frac{4k_B T}{\omega_0 k Q}\frac{1}{[1-(\omega/\omega_0)^2]^2 + (\omega/\omega_0 Q)^2} + n_{ds}^2}. \quad \text{(Formula 5)}$$

In the formula, $k_B$, T, and $n_{ds}$ respectively represent a Boltzmann constant, an absolute temperature, and the displacement noise density of a displacement detector.

From Mathematical Formulae (2) and (3), the absolute value of $V_s$ can be obtained by the following Mathematical Formula (6):

[Mathematical Formula 6]

$$|V_s| = \frac{G(2\omega_m)}{G(\omega_m)} \frac{A_1}{A_2} \frac{V_{ac}}{4}. \quad \text{(Formula 6)}$$

In the formula, the sign of $V_s$ becomes positive when a phase difference $\Phi$ of an $\omega_m$ component contained in the electrostatic force $F_{es}$ with respect to an AC bias voltage is 0° (in phase), and becomes negative when the phase difference $\Phi$ is 180° (reverse phase). Ideally, if the lock-in amplifier 123 detects $X_1 = A_1 \cos \Phi_1$, and Mathematical Formula (6) in which $A_1$ is substituted with $X_1$ is used, the value of $V_s$ including the sign can be obtained. In the actual measurement, however, there may arises the influence of noise or phase lag in a bias circuit or in a displacement detection system for a cantilever, or phase lag caused by a dielectric interposed between the probe and the sample 106. Thus, $\cos \Phi_1$ may have an intermediate value other than +1 and −1. This increases an error in the measurement result. It is therefore more desirable to obtain the absolute value by Mathematical Formula (6), and determine the sign based on the sign of $X_1$. In other words, $V_s$ can be obtained by the following Mathematical Formula (7):

[Mathematical Formula 7]

$$V_s = sgn(X_1) \frac{G(2\omega_m)}{G(\omega_m)} \frac{A_1}{A_2} \frac{V_{ac}}{4}. \quad \text{(Formula 7)}$$

If $X_1$, $A_1$, and $A_2$ are recorded while the probe being scanned in a direction horizontal to the surface of the sample 106, the surface potential image of the sample 106 can be obtained from these values. In addition, $X_1$ is only required for identifying the sign of $V_s$. It is therefore not necessary to perform measurement at every position on the surface of the sample 106. For example, if the polarity of the potential difference between the surface of the sample 106 and a probe electrode 104 is not reversed on every surface of the sample 106, a signal detector 218 is only required to measure $X_1$ at any one position. If the potential calculation unit 219 determines the sign of the measured $X_1$ only once, thereafter, the sign of $V_s$ at all the measurement points can be determined.

The corrosion resistance evaluation device according to the present embodiment includes a database 220 storing the relation between the surface potential difference in the microstructure of a metal with various compositions in a specific liquid, and the corrosion rate of the crevice corrosion or the corrosion rate of the pitting. The arithmetic processing unit 219 calculates the surface potentials of the microstructure on the basis of the surface potential distribution of the metal that has been measured by the OL-EPM. The corrosion rate of a metal under evaluation is predicted on the basis of the maximum surface potential from among the calculated surface potentials, and the relation between the surface potential difference and the corrosion rate of the crevice corrosion or the pitting that is stored in the database 220. The prediction result is displayed on a display device 221. The arithmetic processing unit 219 corresponds to a prediction means of the present invention. In addition, information such as the surface potential distribution and the shape image of the metal that have been measured by the OL-EPM, and the surface potential difference in the microstructure is also displayed on the display device 221. In addition, in FIG. 1, a single arithmetic processing unit serves as a means for measuring the surface potential by calculating a signal from the OL-EPM, and a means for predicting the corrosion rate. These means may be separately provided.

The OL-EPM described in FIG. 1 calculates the surface potential by utilizing the respective magnitudes $A_1$ and $A_2$ of the $\omega_m$ component and the $2\omega_m$ component of the vibration in the cantilever 105 that is caused by electrostatic interacting force. This is called a single frequency (SF) mode.

Next, a modified example of an OL-EPM will be described. In the OL-EPM using the SF mode as illustrated in FIG. 1, the potential may fail to be accurately measured when the ion concentration of a liquid solution becomes higher. Specifically, if the ion concentration of the liquid solution becomes higher, an optimum modulating frequency ($\omega_m$) that can suppress unnecessary interacting force generated in the probe due to unnecessary electrochemical reaction or ion rearrangement increases. Thus, the measurement in a highly-concentrated electric field liquid solution requires an AC bias voltage having very high $\omega_m$. The OL-EPM detects electrostatic interacting force as the displacement of a cantilever that is caused by the electrostatic interacting force. Nevertheless, a displacement sensitivity $G(\omega)$ of the cantilever with respect to the force varies depending on $\omega$. As indicated in Mathematical Formula (4), $G(\omega)$ becomes 1/k on the low frequency side and indicates a peak value at the resonance frequency ($f_0$) of the cantilever, and after the peak, converges to 0 as the frequency becomes higher. Thus, $\omega_m$ and $2\omega_m$ need to have values lower than the value of $f_0$, for detecting the $A_1$ and $A_2$ of sufficient signal intensity. Nevertheless, the value of $f_0$ in a liquid of a currently commercially-available cantilever is 1 MHz or less at the highest. Higher resonance frequency will be achieved in the future due to the downsizing of cantilevers, but there is a physical limit on such higher resonance frequency. Thus, if an AC bias voltage having very high frequency $\omega_m$ required for the measurement in the highly-concentrated liquid solution is used, $2\omega_m$ largely exceeds $f_0$, making it difficult to detect $A_2$. As a result, the potential $V_s$ cannot be calculated.

As a solution for this problem, it is desirable to use an OL-EPM using a dual frequency (DF) mode.

Figure 2:
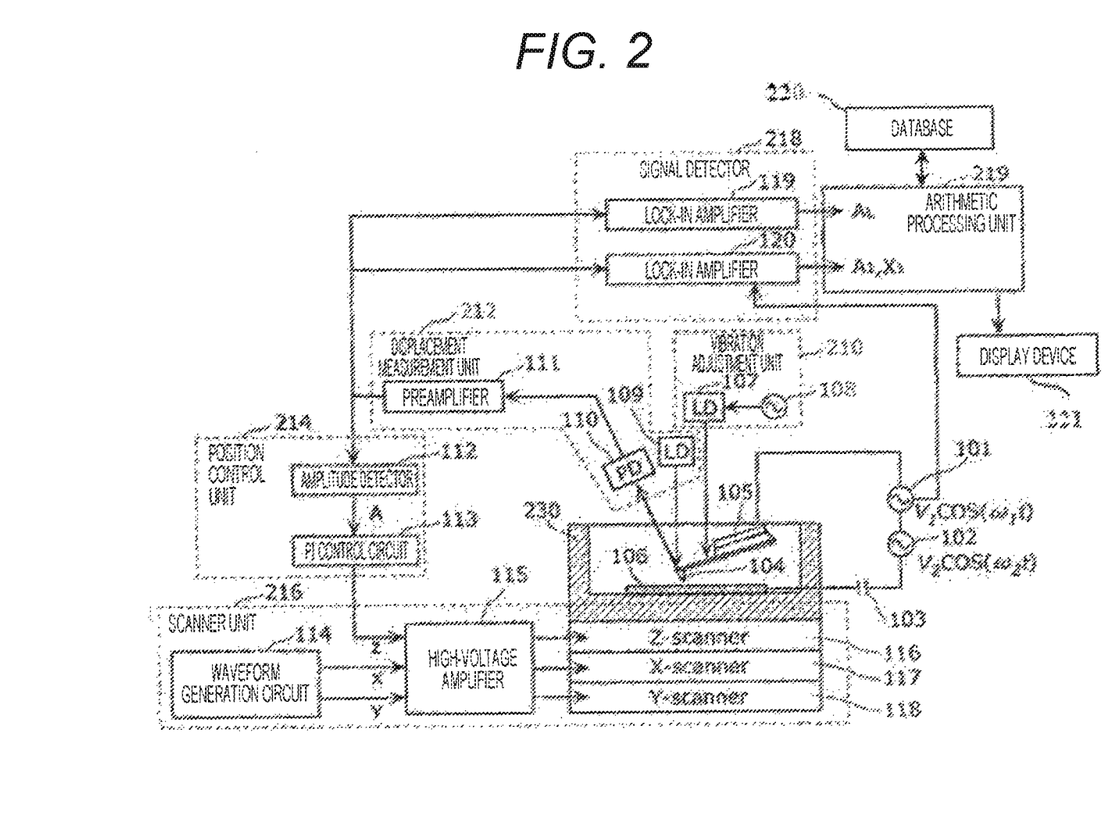
FIG. 2 is a configuration diagram illustrating an evaluation device using an OL-EPM using a dual frequency mode used in the present invention.

FIG. 2 illustrates a configuration diagram of a corrosion resistance evaluation device using an OL-EPM using the DF mode. In addition, the corrosion resistance evaluation device has a similar configuration except that the configuration of the OL-EPM is changed from the SF mode to the DF mode. Thus, a prediction means of a corrosion rate using the database 220, the arithmetic processing unit 219, and the display device 221 remains the same.

The OL-EPM using the DF mode will be described below. As illustrated in FIG. 2, the OL-EPM using the DF mode includes a first alternating-current source 101, a second alternating-current source 102, the capacitor 103, the probe electrode 104, the cantilever 105, a vibration adjustment unit 210, a displacement measurement unit 212, a position control unit 214, a scanner unit 216, the signal detector 218, the potential calculation unit 219, and a sample holder 230.

The first alternating-current source 101 applies a first AC voltage $V_1 \cos(\omega_1 t)$ between the probe electrode 104 and the sample 106.

The second alternating-current source 102 applies, between the probe electrode 104 and the sample 106, a second AC voltage $V_2 \cos(\omega_2 t)$ having a frequency different from a frequency $\omega_1$ of the first AC voltage $V_1 \cos(\omega_1 t)$, in addition to the first AC voltage $V_1 \cos(\omega_1 t)$. In other words, the OL-EPM applies, between the probe electrode 104 and the sample 106, a bias voltage $(V_1 \cos(\omega_1 t)+V_2 \cos(\omega_2 t))$ obtained by adding up the AC voltages having different frequencies. At this time, the electrostatic interacting force $F_{es}$ can be obtained by the following Mathematical Formula (8), using $V_{ts}=V_s-[V_1 \cos(\omega_1 t)+V_2 \cos(\omega_2 t)]$:

[Mathematical Formula 8]

$$F_{es} = \frac{1}{2}\frac{\partial C_{ts}}{\partial z}[V_s - \{V_1\cos(\omega_1 t) + V_2\cos(\omega_2 t)\}]^2$$
$$= \frac{1}{2}\frac{\partial C_{ts}}{\partial z}\left[\left(V_s^2 + \frac{1}{2}V_1^2 + \frac{1}{2}V_2^2\right) - 2V_s[V_1\cos(\omega_1 t) + V_2\cos(\omega_2 t)] +\right.$$
$$\frac{1}{2}[V_1^2\cos(2\omega_1 t) + V_2^2\cos(2\omega_2 t)] +$$
$$\left. V_1 V_2[\cos\{(\omega_1 + \omega_2)t\} + \cos\{(\omega_1 - \omega_2)t\}]\right]$$

As seen from the formula, the electrostatic interacting force $F_{es}$ is proportional to the square of the potential difference between the probe electrode 104 and the sample 106. Thus, the electrostatic interacting force $F_{es}$ contains a plurality of frequency components. The plurality of frequency components includes an $\omega_1-\omega_2$ component having a frequency equivalent to the difference between the two frequencies $\omega_1$ and $\omega_2$. For example, when $\omega_1=1$ MHz+30 kHz, and $\omega_2=1$ MHz, $\omega_1-\omega_2=30$ kHz. In other words, regardless of the values of $\omega_1$ and $\omega_2$, the difference therebetween can be set to a low frequency that enables signal detection with sufficient sensitivity.

The OL-EPM illustrated in FIG. 2 utilizes the $\omega_1-\omega_2$ ($=\omega_L$) component instead of the $2\omega_m$ component (equivalent to the $2\omega_1$ component in the DF mode) in the SF mode in FIG. 1, so that the surface potential $V_s$ of a sample can be determined even when a high-frequency AC bias voltage is applied.

In the OL-EPM illustrated in FIG. 2, the capacitor 103 is a capacitor for removing a direct-current component that can be contained in the superimposed voltage of the first alternating-current source 101 and the second alternating-current source 102.

The probe electrode 104 is made of conductive material. Specifically, the probe electrode 104 is a probe electrode having a shape with a sharply-pointed leading end.

The cantilever 105 has the probe electrode 104 at the leading end. One end of both ends of the cantilever 105 that has the probe electrode 104 is a fee end, and the other end is a fixed end. Examples of material include silicon and silicon nitride. In addition, the material coated with a conductive metal such as gold and platinum may be used. In the present embodiment described below, the cantilever 105 is assumed to be a cantilever made of silicon coated with gold.

The vibration adjustment unit 210 excites the cantilever 105 at a frequency ($f_d=(\omega_d/2\pi)$) near the resonance frequency of the cantilever 105. The vibration adjustment unit 210 according to the present embodiment excites the cantilever 105 using a so-called photothermal excitation method. More specifically, the vibration adjustment unit 210 includes an LD 107 and an excitation alternating-current source 108 for driving the LD 107. The LD 107 emits an intensity-modulated laser beam onto the back surface of the cantilever 105 made of silicon coated with gold. The cantilever 105 irradiated with the intensity-modulated laser beam is excited because the coefficients of thermal expansion of gold and silicon are different.

The displacement measurement unit 212 outputs a voltage corresponding to the interacting force between the probe electrode 104 and the sample 106. Specifically, the displacement measurement unit 212 measures the displacement in the z-axis direction of the leading end of the cantilever 105. The displacement measurement unit 212 measures the interacting force generated between the probe electrode 104 and the sample 106, in association with the displacement of the leading end of the cantilever 105. The displacement of the leading end of the cantilever 105 is also used by the scanner unit 216 to be described later, for performing position control for keeping the distance between the sample 106 and the probe electrode 104 constant.

More specifically, the displacement measurement unit 212 includes the LD 109, the PD 110, and the preamplifier 111. The displacement measurement unit 212 receives, by the PD 110, the reflected light of a semiconductor laser beam emitted from the LD 109 onto the leading end of the cantilever 105. In accordance with the displacement in the z-axis direction of the leading end portion of the cantilever 105, a semiconductor laser beam reception position of the PD 110 changes. By extracting the change (shift) in light reception position via the preamplifier 111 as a voltage change amount, the displacement measurement unit 212 outputs a voltage corresponding to the interacting force between the probe electrode 104 and the sample 106.

The position control unit 214 performs feedback control for the scanner unit 216 so as to keep the vibration amplitude of the cantilever 105 constant. If the distance between the probe electrode 104 and the surface of the sample 106 changes due to the unevenness on the surface of the sample 106, the magnitude of the interacting force exerted between the probe electrode 104 and the sample 106 changes. As a result, the vibration amplitude of the cantilever 105 being excited by the vibration adjustment unit 210 and vibrating at a constant vibration amplitude changes. Thus, by controlling the distance between the probe electrode 104 and the sample 106 so as to keep the vibration amplitude of the cantilever 105 constant, the distance between the probe electrode 104 and the sample 106 can be kept constant.

The position control unit 214 includes an amplitude detector 112 and a proportional-integral (PI) control circuit 113. The amplitude detector 112 acquires the displacement of the leading end portion of the cantilever 105 from the displacement measurement unit 212. Then, the amplitude detector 112 detects the vibration amplitude of the cantilever 105 on the basis of the acquired displacement.

The PI control circuit 113 outputs a control signal for causing the scanner unit 216 to adjust the height (z-axis direction) of the sample holder 230, so as to keep the vibration amplitude detected by the amplitude detector 112 constant. In addition, another feedback control circuit may be used instead of the PT control circuit 113.

In addition, a control signal for adjusting the z-axis direction is output in accordance with the unevenness on the surface of the sample 106. Thus, by recording the value of the control signal, a physical form (information about the height direction) of the surface of the sample 106 can be measured. Accordingly, together with the surface potential distribution obtained through the potential measurement, the shape image of the sample surface can also be obtained.

In the present embodiment, the position control unit 214 may control the distance between the probe electrode 104 and the sample 106 so as to keep the resonance frequency or the phase of the cantilever constant, instead of the vibration amplitude of the cantilever 105.

In other words, the position control unit 214 adjusts the distance between the surface of the sample 106 and the probe electrode 104 so that the change in the distance between the probe electrode 104 and the sample 106 becomes constant. In addition, the amount by which the distance is adjusted may be output as the height information of the surface of the sample 106.

The scanner unit 216 moves the position of the sample holder 230 by 1 nm to 1 mm in three axis directions orthogonal to one another, i.e., x-, y-, and z-axis directions. As described above, the movement in the z-axis direction is performed for keeping the vibration amplitude of the cantilever 105 constant. The movements in the x-axis and y-axis directions are performed for planarly and consecutively measuring the physical form and the potential distribution on the sample 106. In particular, the movement amount in the x-axis and y-axis directions is preferably set to 100 μm or more. With this movement amount, the surface potential can be measured even for the metal structure having crystal grains of 100 μm or more.

The scanner unit 216 includes a waveform generation circuit 114, a high-voltage amplifier 115, a Z-scanner 116, an X-scanner 117, and a Y-scanner 118.

The Z-scanner 116 moves the sample holder 230 in the z-axis direction. The X-scanner 117 moves the sample holder 230 in the x-axis direction. The Y-scanner 118 moves the sample holder 230 in the y-axis direction.

The OL-EPM amplifies, by the high-voltage amplifier 115, the control signal (z-axis direction) output from the position control unit 214 as a result of feedback control, and a signal for scanning in a planar direction (x-axis and y-axis directions) that has been generated by the waveform generation circuit 114. Then, the OL-EPM outputs the amplified signals to a scanner corresponding to an axis in which movement is to be performed, among the Z-scanner 116, the X-scanner 117, and the Y-scanner 118.

The signal detector 218 outputs the magnitude of a specific frequency component contained in the voltage output by the displacement measurement unit 212. More specifically, the signal detector 218 outputs, to the arithmetic processing unit 219, (1) the magnitude and the phase of a frequency component having the same frequency as the frequency $\omega_1$ of the first AC voltage, and (2) the magnitude of a frequency component having the same frequency as the difference between the frequency $\omega_1$ of the first AC voltage and the frequency $\omega_2$ of the second AC voltage (i.e., $\omega_1-\omega_2$), among voltages output by the displacement measurement unit 212.

Specifically, the signal detector 218 is a highly-sensitive AC voltmeter. For example, a lock-in amplifier or the like can be used as the signal detector 218. The signal detector 218 according to the present embodiment includes lock-in amplifiers 119 and 120. The signal detector 218 uses AC voltage output by the first alternating-current source 101, as a reference signal. The signal detector 218 detects $X_1$, $A_1$, and $A_L$ from among voltage signals output from the displacement measurement unit 212. In addition, as described later, the potential measurement device 100 does not always have to detect the $X_1$.

The arithmetic processing unit 219 calculates the surface potential of the sample 106 from the value output from the signal detector 218. More specifically, the potential calculation unit 219 calculates the surface potential $V_s$ of the sample 106 using (1) the magnitude $A_1$ of the frequency component having the same frequency as the frequency $\omega_1$ of the first AC voltage among voltages output by the displacement measurement unit 212, (2) the amount $X_1$ obtained by multiplying, by $A_1$, the cosine value of the phase difference between the frequency component having the same frequency as the frequency $\omega_1$ and the first AC voltage among voltages output by the displacement measurement unit 212, (3) the magnitude $A_L$ of the frequency component having the same frequency as the difference between the frequency $\omega_1$ of the first AC voltage and the frequency $\omega_2$ of the second AC voltage among voltages output by the displacement measurement unit 212, (4) the vibration amplitude $V_2$ of an AC voltage output by the second alternating-current source, and (5) the transfer function $G(\omega)$ of the cantilever 105 to which the probe electrode 104 is attached at the free end thereof, by the formula $V_s$=sgn $(X_1) \times (\omega_1-\omega_2)/G(\omega_1) \times (A_1/A_L) \times (V_2/2)$.

In addition, the arithmetic processing unit 219 may output the surface potential image of the sample 106 by arranging the calculated surface potentials in accordance with the x-y plane scanned by the scanner unit 216.

Next, the description will be given of the principle in which the potential measurement device according to the present invention measures the surface potential of a sample in a liquid, using the OL-EPM illustrated in FIG. 2 as a specific example.

The respective magnitudes $A_1$ and $A_L$ of the $\omega_1$ component and the $\omega_1-\omega_2$ ($=\omega_L$) component that are contained in a cantilever displacement signal output from the displacement measurement unit 212 are indicated by the following Mathematical Formulae (9) and (10), respectively, considering the transfer function $G(\omega)$ of the cantilever:

[Mathematical Formula 9]

$$A_1 = G(\omega_1)\left|\frac{\partial C_{ts}}{\partial z}V_s V_1\right|, \text{ and} \quad \text{(Formula 9)}$$

[Mathematical Formula 10]

$$A_L = G(\omega_L)\left|\frac{\partial C_{ts}}{\partial z}\frac{V_1 V_2}{2}\right|. \quad \text{(Formula 10)}$$

In these formulae, $A_1$, $A_L$, $G(\omega_1)$, and $G(\omega_L)$ can be obtained in a similar manner to that in the above-described OL-EPM using the SF mode. From these values, the arithmetic processing unit 219 can obtain the absolute value of $V_s$ by the following formula:

[Mathematical Formula 11]

$$|V_s| = \frac{G(\omega_L)}{G(\omega_1)}\frac{A_1}{A_L}\frac{V_2}{2}. \quad \text{(Formula 11)}$$

In addition, the sign of $V_s$ can also be determined in a similar manner to that in the OL-EPM using the SF mode. Thus, the arithmetic processing unit 219 can obtain $V_s$ by the following Mathematical Formula (12):

[Mathematical Formula 12]

$$V_s = sgn(X_1)\frac{G(\omega_L)}{G(\omega_1)}\frac{A_1}{A_L}\frac{V_2}{2}. \quad \text{(Formula 12)}$$

In addition, $X_1$ is only required for identifying the sign of $V_s$. It is therefore not necessary to perform measurement at every position on the surface of the sample 106. For example, if the polarity of the potential difference between the surface of the sample 106 and the probe electrode 104 is not reversed on every surface of the sample 106, the signal detector 218 is only required to measure $X_1$ at any one position. If the potential calculation unit 219 determines the sign of the measured $X_1$ only once, thereafter, the sign of $V_s$ at all the measurement points can be determined.

In addition, functions and configurations of the vibration adjustment unit 210, the displacement measurement unit 212, the position control unit 214, and the scanner unit 216 have been described using FIG. 2. The same applies to the OL-EPM illustrated in FIG. 1.

As described above, by using an OL-EPM, the potential distribution of a metal can be measured in nanoscale even under in-liquid environment, and the potential difference in the microstructure of the metal can be measured.

The present inventors have found out that, by measuring the local potential distribution of a duplex phase stainless steel placed in a water solution, using an OL-EPM, the corrosion resistance of the stainless steel can be evaluated on the basis of the potential difference between the ferrite phase (α phase) and the austenite phase (γ phase) that has been obtained through the measurement. This is not limited to stainless steel, and is applicable to the potential difference between a precipitate and a mother phase in any metal structure. Such evaluation is realized only if an OL-EPM is used. As corrosion evaluation, an immersion test of immersing a metal in a corrosion liquid solution under usage environment for a long time, i.e., half year to one year to determine the corrosion depth is often employed. By utilizing an OL-EPM as an alternative method of such an immersion test, the time taken for the development of new metal material can be substantially shortened. Furthermore, only by measuring the surface potential in a specific liquid, the qualitative and quantitative determination of a precipitate in the metal structure can be easily performed.

According to the evaluation method of the present invention, the rate of micro corrosion that cannot be recognized by macro corrosion evaluation, i.e., the rate of corrosion can be accurately estimated under the usage environment, the rate of corrosion attributed to galvanic corrosion arising from the potential difference between a precipitate generated at the grain boundary of a structure and the periphery of the precipitate, and furthermore, between the precipitate and a base material, and galvanic corrosion arising from the potential difference between two structures in duplex phase stainless steel. The corrosion rate evaluation enables the estimation of lifetimes of pipes and pumps, so that the replacement timing can be predicted. Thus, the evaluation method can contribute to stable operation of plants. In addition, an immersion test of immersing a test piece of a metal for a long time, i.e., half year to one year to determine the corrosion depth is often employed. Nevertheless, according to the evaluation method, the corrosion depth can be determined in a short period of time of several hours, so that the time taken for the development of new metal material can be substantially shortened.

Meanwhile, the surface potential difference in the microstructure of a metal in a specific liquid is constant, and by applying the above-described corrosion resistance evaluation device, the composition of a precipitate precipitated in the metal structure of metal material can be predicted. In other words, the database 220 prestores data on the surface potential difference between the surface potential of a metal with various compositions, and the surface potential of a reference metal. For a metal under evaluation, the surface potential difference from the reference metal is measured using an OL-EPM. Then, by comparing with the data in the database, the composition of the precipitate precipitated in the metal structure of metal material can be predicted.

In metal, it is known that, if a precipitate of a specific composition is generated, corrosion easily occurs. Thus, the qualitative and quantitative determination of a precipitate is essential for evaluating metal corrosiveness. In general, for identifying the precipitate composition in the metal structure, a method of extracting a part of the precipitate from the material, and analyzing the extracted part using a scanning electron microscope or a transmission electron microscope is employed. In this case, the method involves the work of searching for the location where the precipitate exists, and the time is taken for extracting only the part where the precipitate exists. In contrast, according to the method of the present invention, the composition of the precipitate can be predicted only by measuring the surface potential in a specific liquid, very simple identification method and quantitative determination method of a precipitate can be provided.

The detailed description will be given below using examples.

Example 1

In Example 1, the description will be given of an example in which the surface potential of the metal was measured using the OL-EPM using the SF mode as illustrated in FIG. 1. The duplex phase stainless steel was used as a measurement sample, and the potential distribution was observed in the 10 mM of NaCl water solution. The sample 106 is placed in a sample holder in a state in which the sample 106 is immersed in the NaCl water solution 122. The sample 106 is made nonconductive and connected to the cantilever 105 via the capacitor 103 and the alternating-current source 121. Using the photothermal excitation method (the method of emitting an intensity-modulated laser beam onto the back surface of a cantilever made of silicon coated with gold, and exciting the cantilever by utilizing the difference in coefficient of thermal expansion between gold and silicon), the cantilever 105 was excited at a frequency (1-1.2 MHz) near the resonance frequency of the cantilever 105. The distance between the probe 104 and the sample 106 was controlled so as to keep the vibration amplitude A of the cantilever 105 constant. The reflected light of a laser beam generated from a laser generator (LD) 109 and emitted onto the back surface of the cantilever 105 is detected by a detector (PD) 109.

Based on the position of the reflected light detected by the detector 109, the amount of displacement in the Z direction of the cantilever 105 is measured by the preamplifier 111, and input to the lock-in amplifier 123. The alternating-current source 121 applies, between the sample 106 and the cantilever 105, an AC ($V_{ac} \cos(\omega_m t)$) bias voltage having a modulating frequency $f_m$ ($=\omega_m/2\pi$). In this example, a high-frequency AC bias voltage of 10 kHz was applied. When the frequency is 10 kHz or less, the alteration of the sample was observed. Thus, it is desirable to select a high frequency of 10 kHz or more. The AC ($V_{ac} \cos(\omega_m t)$) signal is input to the lock-in amplifier 123, and the respective magnitudes $A_1$ and $A_2$ of the $\omega_m$ and $2\omega_m$ components contained in the electrostatic force $F_{es}$ are measured. In addition, the lock-in amplifier 123 detects $X_1 = A_1 \cos \Phi 1$ to determine the sign. Furthermore, the surface potential $V_s$ of the sample 106 is obtained by the following Mathematical Formula (13):

[Mathematical Formula 13]

$$V_s = sgn(X_1)\frac{G(2\omega_m)}{G(\omega_m)}\frac{A_1}{A_2}\frac{V_{ac}}{4}. \quad \text{(Formula 13)}$$

The leading end of the cantilever 105 is provided with a probe. It was confirmed that, by scanning the sample surface using the probe, the shape image and the potential image of the sample surface can be simultaneously obtained as two-dimensional data.

Example 2

In Example 2, the description will be given of an example in which the surface potential of the metal was measured using the OL-EPM using the DF mode as illustrated in FIG. 2. The duplex phase stainless steel was used as a measurement sample, and the potential distribution was observed in the 10 mM of NaCl water solution. The sample 106 is placed in the sample holder 230 in a state in which the sample 106 is immersed in the NaCl water solution 122. The sample 106 is made nonconductive and connected to the cantilever 6 via the capacitor 103 and two alternating-current sources 101 and 102. Using the photothermal excitation method (the method of emitting an intensity-modulated laser beam onto the back surface of a cantilever made of silicon coated with gold, and exciting the cantilever by utilizing the difference in coefficient of thermal expansion between gold and silicon), the cantilever 105 was excited at a frequency (1-1.2 MHz) near the resonance frequency of the cantilever 105. The distance between the probe 104 and the sample 106 was controlled so as to keep the vibration amplitude A of the cantilever 105 constant. The reflected light of a laser beam generated from the laser generator (LD) 109 and emitted onto the back surface of the cantilever 105 is detected by the detector (PD) 109.

Based on the position of the reflected light detected by the detector 109, the amount of displacement in the Z direction of the cantilever 105 is measured by the preamplifier 111, and input to the lock-in amplifier 123. The alternating-current sources 101 and 102 applied, between the sample 106 and the cantilever 105, a bias voltage ($V_1 \cos(\omega_1 t) + V_2 \cos(\omega_2 t)$) obtained by adding up AC voltages with different frequencies. The signal is input to the lock-in amplifiers 109 and 120, and the respective magnitudes $A_1$ and $A_L$ of the $\omega_1$ and $\omega_L$ components contained in the displacement signal of the cantilever 105 are measured by utilizing the $\omega_1-\omega_2$ ($=\omega_L$) component instead of the $2\omega_m$ component in the SF mode (equivalent to the $2\omega_1$ component in the DF mode). In addition, the lock-in amplifier 120 detects $X_1 = A_1 \cos\Phi 1$ to determine the sign. Furthermore, the surface potential $V_s$ is obtained by the following Mathematical Formula (14):

[Mathematical Formula 14]

$$V_s = sgn(X_1)\frac{G(\omega_L)}{G(\omega_1)}\frac{A_1}{A_L}\frac{V_2}{2}. \quad \text{(Formula 14)}$$

The leading end of the cantilever 105 is provided with a probe. It was confirmed that, by scanning the sample surface using the probe, the shape image and the potential image of the sample surface can be simultaneously obtained as two-dimensional data.

Example 3

The description will be given of an example in which corrosion resistance evaluation was conducted using the corrosion resistance evaluation device using the OL-EPM using the DF mode as illustrated in FIG. 2.

Similarly to Example 2, a bias voltage obtained by adding up two frequency components $\omega_1$ (=700-800 kHz) and $\omega_2$ ($\omega_1+30$ kHz) was applied between the probe 104 and the sample 106. The capacitor 103 was inserted so that a DC bias current does not flow between the probe 106 and the sample 05. $A_1$ and $A_L$ are detected from the displacement signal of the cantilever 105, using the two lock-in amplifiers 119 and 120. Using the photothermal excitation method (the method of emitting an intensity-modulated laser beam onto the back surface of a cantilever made of silicon coated with gold, and exciting the cantilever by utilizing the difference in coefficient of thermal expansion between gold and silicon), the cantilever 105 was excited at a frequency (1-1.2 MHz) near the resonance frequency of the cantilever 105. The distance between the probe 104 and the sample 106 was controlled so as to keep the vibration amplitude A of the cantilever 105 constant.

Next, potential distributions of three types of duplex phase stainless steels (LDX2101, 2205, and 2507) were measured. In these duplex phase stainless steels, contents of Cr, Mo, and N are larger, and pitting resistance and strength are higher in the order of LDX2101, 2205, and 2507. Those having sufficiently-polished surfaces were used for the measurement.

Figure 3A:
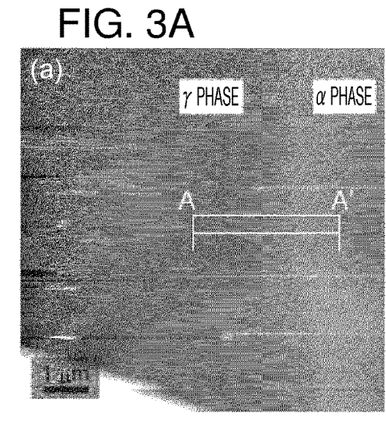
FIGS. 3A to 3C are diagrams illustrating a result obtained by simultaneously observing a surface shape and a potential distribution of an LDX2101.
Figure 3B:
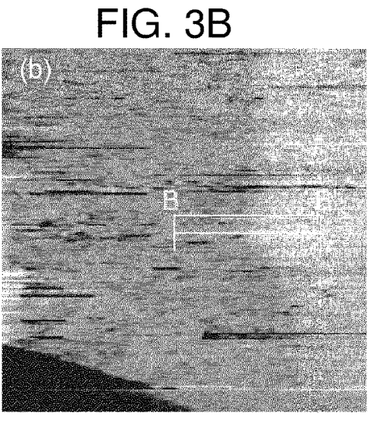
Figure 3C:
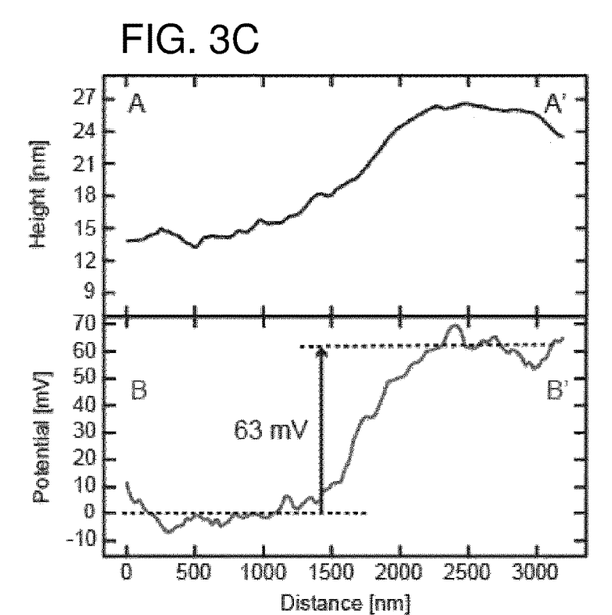

FIGS. 3(a) to 3(c) illustrate a result obtained by simultaneously observing the surface shape and the potential distribution of the LDX2101. The DF mode was used for the measurement, and the measurement was conducted under the condition in which two modulating frequencies and AC bias voltages were set to 800 kHz/1 V and 830 kHz/1 V. It is known that, when the surface of the duplex phase stainless steel is viewed using an optical microscope, a sea-island shape is observed, and the austenite phase (γ phase) appears in an island shape while the ferrite phase (α phase) appears in a sea shape. When the boundary portion of the phases was observed, regions having different heights were seen. In general, since a γ phase has higher processability and is more easily polished as compared with an α phase, the γ phase has lower height than the α phase. Thus, from the shape image (FIG. 3(a)), it can be seen that the left side is the γ phase and the right side is the α phase. Also in the potential distribution image illustrated in FIG. 3(b), the contrast changes at the boundary, showing that the potentials are different between the α phase and the γ phase. FIG. 3(c) illustrates an average value of the line distribution of portions defined by white lines in the shape image and the potential image. In the distribution, the potential difference of the α phase with respect to the γ phase was approximately +63 mV at the most.

Figure 4A:
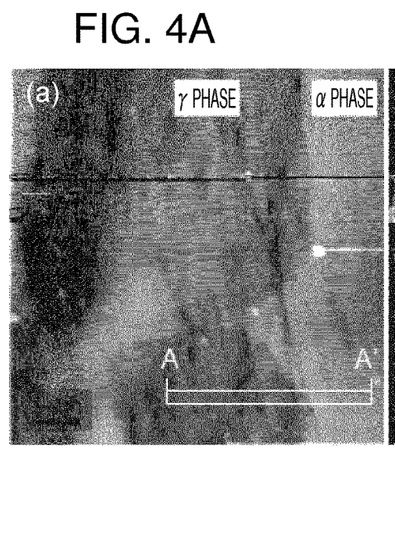
FIGS. 4A to 4C are diagrams illustrating a result obtained by simultaneously observing a surface shape and a potential distribution of a 2205.
Figure 4B:
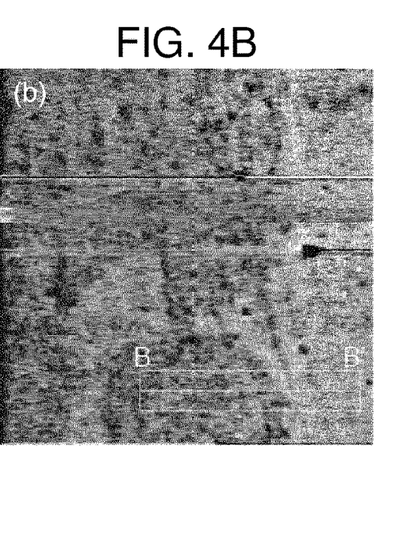
Figure 4C:
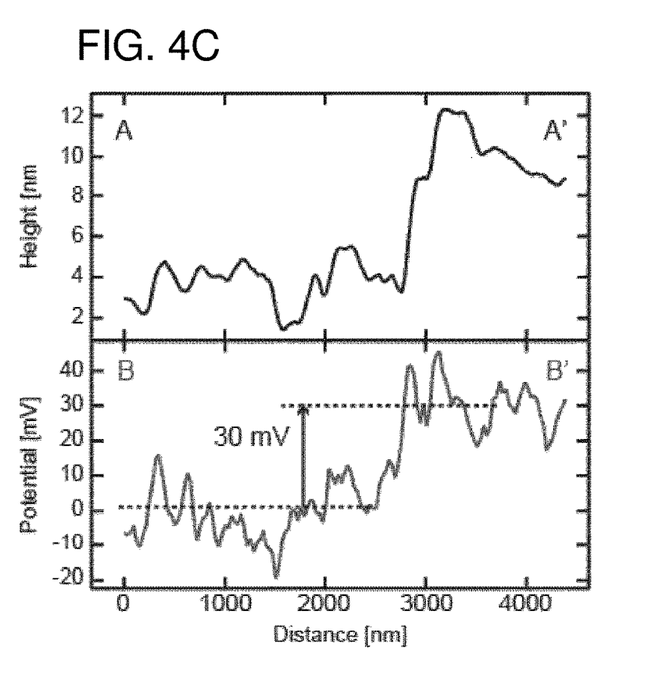

Similarly, FIGS. 4(a) to 4(c) illustrate a result obtained by measuring the surface structure and the potential distribution of the 2205. The DF mode was used for the measurement, and the measurement was conducted under the condition in which two modulating frequencies and AC bias voltages were set to 700 kHz/1 V and 730 kHz/1 V. Similarly to the LDX2101, the difference in height was observed at the boundary between the α phase and the γ phase, and it can be seen that the left side in FIG. 4(a) is the γ phase and the right side is the α phase. Also in the potential distribution image illustrated in FIG. 4(b), the contrast changes at the boundary, showing that the potentials are different between the α phase and the γ phase. FIG. 4(c) illustrates an average value of the line distribution of portions defined by white lines in the shape image and the potential image. In the distribution, the potential difference of the α phase with respect to the γ phase was approximately +30 mV at the most.

Figure 5A:
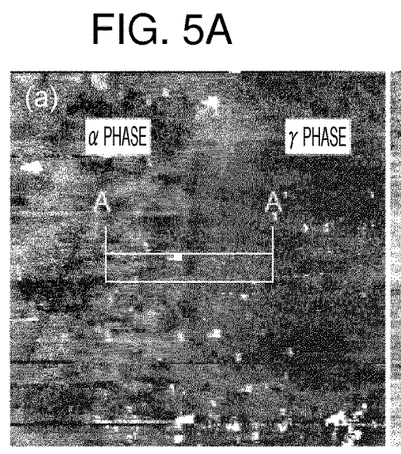
FIGS. 5A to 5C are diagrams illustrating a result obtained by simultaneously observing a surface shape and a potential distribution of a 2507.
Figure 5B:
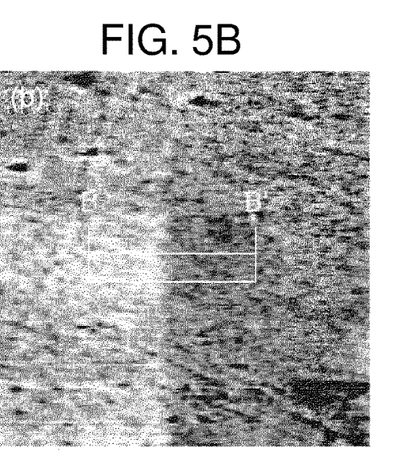
Figure 5C:
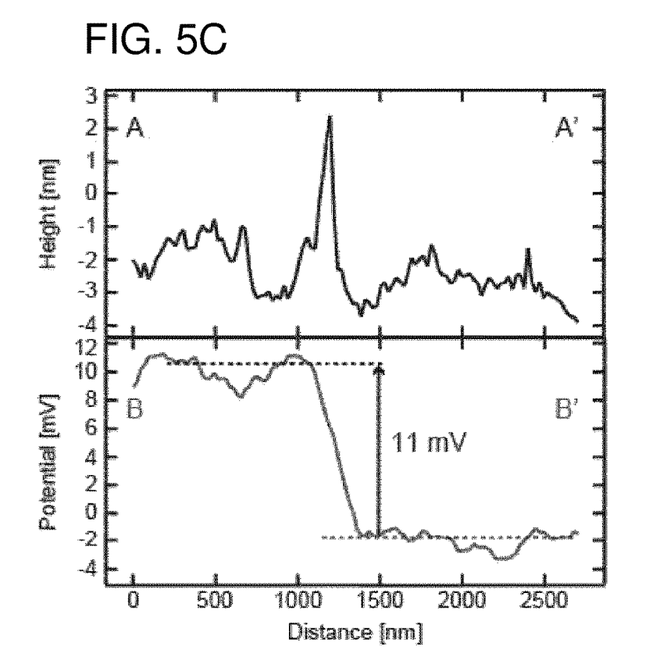

FIGS. 5(a) and 5(b) illustrate the surface shape image and the potential distribution image of the 2507. The DF mode was used for the measurement, and the measurement was conducted under the condition in which two modulating frequencies and AC bias voltages were set to 800 kHz/1 V and 830 kHz/1 V. From the difference in height, it can be seen that the left side is the α phase and the right side is the γ phase. Also in the potential distribution image illustrated in FIG. 5(b), the contrast changes at the boundary, showing that the potentials are different between the α phase and the γ phase. FIG. 5(c) illustrates an average value of the line distribution of portions defined by white lines in the shape image and the potential image. In the distribution, the potential difference of the α phase with respect to the γ phase was approximately +11 mV.

From these results, it was found out that the surface potential differences in the microstructure become smaller in the order of LDX2101>2205>2507.

Figure 6:
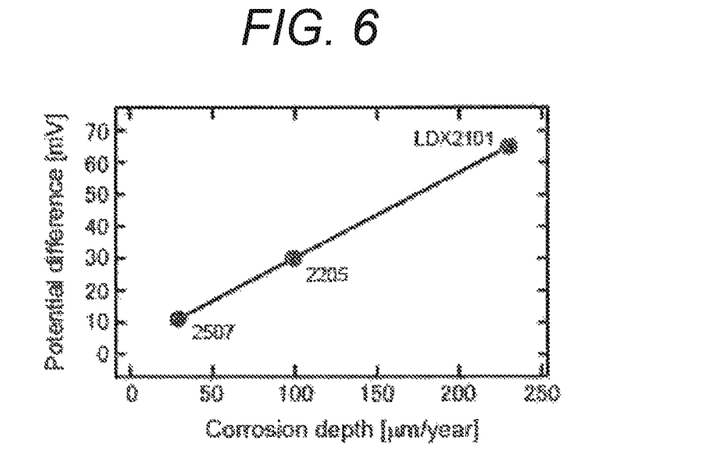
FIG. 6 is a diagram illustrating a relation between a corrosion rate of a crevice corrosion of each duplex phase stainless steel and a potential difference between an α phase and a γ phase.

FIG. 6 is a plot illustrating the relation between the crevice corrosion depth of each duplex phase stainless steel that was obtained by conducting an immersion test using seawater for one year, and the potential difference between the α phase and the γ phase that was obtained as described above. Such a tendency that the larger the potential difference is, the larger the corrosion depth is was obtained.

One of major corrosions of duplex phase stainless steel is galvanic corrosion. The galvanic corrosion is corrosion that occurs in a state in which dissimilar metals are in contact with each other, and the corrosion of the metal surface with low electrode potential is promoted. The corrosion of a metal having different compositions as in duplex phase stainless is closely related to such galvanic corrosion. It can be therefore seen that the potential difference between two phases that was measured using the OL-EPM is attributed to the galvanic corrosion, and the potential difference between electrodes is related to corrosiveness.

The relation between the surface potential difference in the metal structure with various compositions and the crevice corrosion depth was stored in a database. Next, the maximum surface potential difference in the structure of a duplex phase stainless of which the level of corrosion is unknown was measured. Referring to the data in the database, the crevice corrosion depth of a year was estimated on the basis of the measured surface potential difference. Based on the estimated crevice corrosion depth, the period of time until a pit is generated in a metal pipe can be estimated.

Figure 7:
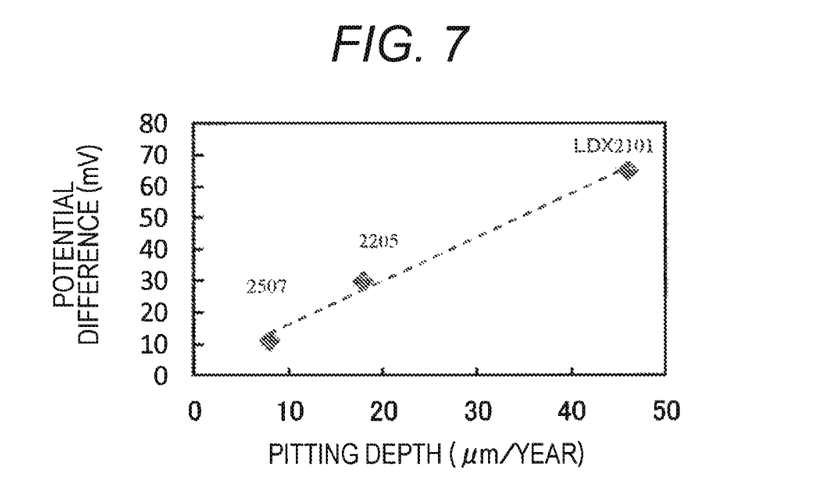
FIG. 7 is a diagram illustrating a relation between a corrosion rate of a pitting of each duplex phase stainless steel and a potential difference between an α phase and a γ phase.

Through the above procedures, a similar tendency is obtained not only for the crevice corrosion but also for the pitting depth. FIG. 7 is a plot illustrating the relation between the pitting depth of each duplex phase stainless steel that was obtained by conducting a spray test using salt water for one year, and the potential difference between the α phase and the γ phase that was obtained as described above. Such a tendency that the larger the potential difference is, the larger the pitting depth is was obtained. The relation between the surface potential difference in the metal structure with various compositions and the pitting depth was stored in a database. Next, the maximum surface potential difference in the structure of a duplex phase stainless of which the level of corrosion is unknown was measured. Referring to the data in the database, the pitting depth of a year was estimated on the basis of the measured maximum surface potential difference. Based on the estimated pitting depth, the period of time until a pit is generated in a metal pipe can be estimated.

Example 4

Metal material being used in an actual plant machine was extracted, and the surface potential was measured similarly to Example 3. The measurement result data was obtained as a surface potential distribution. Based on the data, the maximum potential difference in the surface potential distribution was determined. Referring to the data in the database, a crevice corrosion depth obtainable after the immersion of a certain period of time was estimated on the basis of the measured maximum potential difference. Subsequently, the corrosion rate was estimated. Based on the thickness of the metal being used in the actual plant machine, a period of time until the metal is penetrated was calculated, and a replacement timing was predicted. These prediction means were all executed in the arithmetic processing unit 219.

Example 5

On the plant design stage, material before construction or under construction was extracted, and the surface potential was measured similarly to Example 3. The measurement result data was obtained as a surface potential distribution. Based on the data, the maximum potential difference in the surface potential distribution was determined. Referring to the data in the database, a crevice corrosion depth obtainable after the immersion of a certain period of time was estimated on the basis of the measured maximum potential difference. Subsequently, the corrosion rate was estimated. Based on the thickness of the metal being used in the actual plant machine, a period of time until the metal is penetrated was calculated, and a replacement timing was predicted. These prediction means were all executed through computer control.

Example 6

Similarly to Example 3, the surface potential ($V_{S1}$) of a metal with various compositions was measured using a corrosion resistance evaluation device using the OL-EPM using the DF mode as illustrated in FIG. 2. The measurement was conducted under the condition in which two modulating frequencies and AC bias voltages were set to 800 kHz/1 V and 830 kHz/1 V. Furthermore, the surface potential ($V_{SR}$) of a reference metal was measured at the same time. The data on the surface potential difference ($V_{S1}-V_{SR}$) with respect to the reference metal was acquired in advance, and after the acquired data was compiled into a database, the data was stored in a computer. The surface potential ($V_{SX}$) of a precipitate with an unknown composition was measured using the same method as the above-described method, and the surface potential of the reference metal was measured at the same time. Referring to the data in the database, the composition of a precipitate precipitated in the metal structure was searched for on the basis of the surface potential difference ($V_{S1}-V_{SR}$) with respect to the reference metal. These processes were all controlled by the computer.

Figure 8:
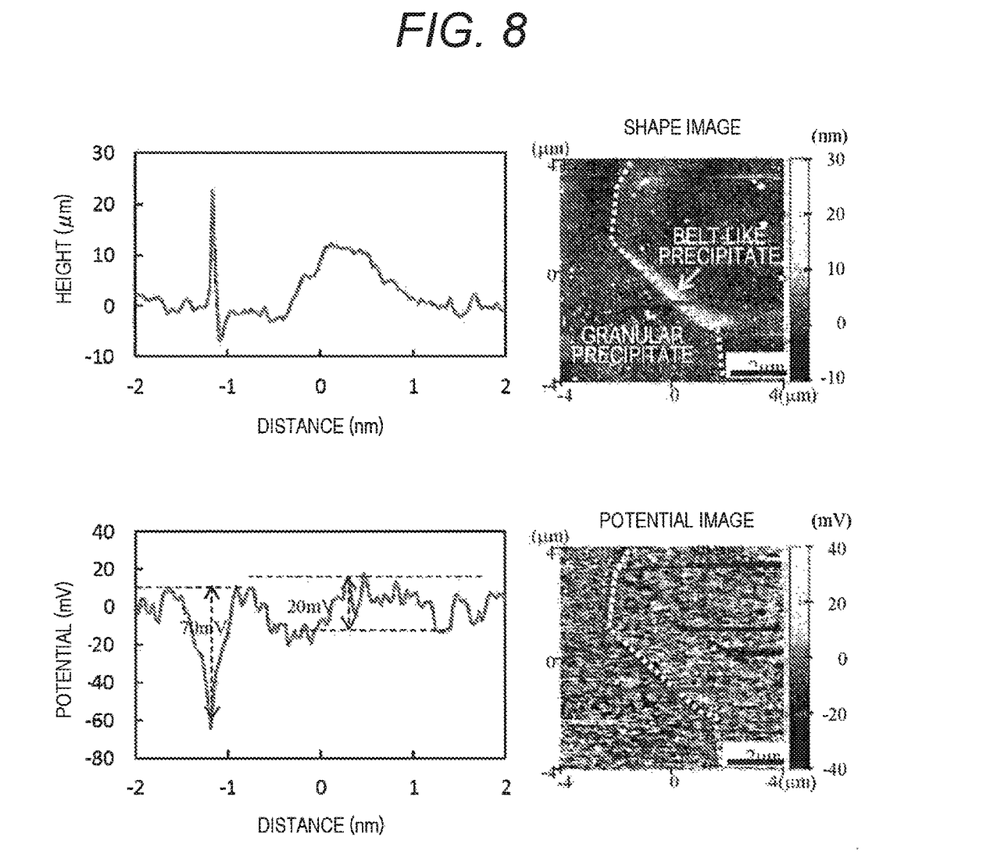
FIG. 8 is a diagram illustrating an example of a measurement result of a shape image and a potential image of a precipitate of an SUS304.

In addition, it was confirmed that the compositions of a plurality of precipitates having the sizes from 1 nanometer to 100 micrometers can be predicted. FIG. 8 illustrates an example of measurement of a shape image and a potential image of a precipitate of an SUS304. A granular precipitate with the maximum potential difference of 70 mV was identified as MnS using a transmission electron microscope. In addition, a plate-like precipitate with the maximum potential difference of 20 mV was identified as $Cr_{23}C_6$ using the transmission electron microscope. In this manner, it was confirmed that the maximum potential difference varies depending on each precipitate composition.

An image processing means is further included. In the image processing, the area of a surface potential region of a specific precipitate is determined on the basis of the result obtained by measuring the surface potential ($V_{S1}$) of a metal in a liquid as an in-surface distribution. This area is calculated as an area ratio (percentage) with respect to the total area. Based on the area ratio, the content of the precipitate precipitated in the metal structure was predicted on the percentage-display basis.

The invention claimed is:

1. A metal corrosion resistance evaluation method comprising:
   measuring a surface potential of a metal under evaluation in a state in which the metal is immersed in a usage-environment liquid to determine a surface potential distribution of the metal;
   calculating surface potential differences in a microstructure of the metal on the basis of the surface potential distribution; and
   predicting a corrosion rate of a crevice corrosion or a corrosion rate of a pitting of the metal using a maximum surface potential difference from among the calculated surface potential differences as an evaluation index for corrosion evaluation,
   wherein, in measurement of a surface potential of the metal, an alternating-current bias voltage is applied between a cantilever including a probe electrode at a leading end, and the metal immersed in the liquid, and a surface potential of the metal surface is calculated by utilizing vibration of the cantilever that is caused by electrostatic interacting force, while scanning the probe electrode in a direction horizontal to the metal surface.

2. The metal corrosion resistance evaluation method according to claim 1,
   wherein a corrosion rate of crevice corrosion or a corrosion rate of pitting of the metal under evaluation is predicted on the basis of a correlation between a maximum surface potential difference and corrosion rates in the liquid of two or more metals with different compositions, of which a corrosion rate of a crevice corrosion depth or a pitting depth in the liquid is known.

3. The metal corrosion resistance evaluation method according to claim 1,
   wherein the metal under evaluation is a stainless steel.

4. A metal corrosion resistance evaluation method comprising:
   measuring a surface potential of a metal under evaluation in a state in which the metal is immersed in a usage-environment liquid to determine a surface potential distribution of the metal;
   calculating surface potential differences in a microstructure of the metal on the basis of the surface potential distribution; and
   predicting a corrosion rate of a crevice corrosion or a corrosion rate of a pitting of the metal using a maximum surface potential difference from among the calculated surface potential differences as an evaluation index for corrosion evaluation,
   wherein a metal extracted from metal material being used in an actual plant machine, or a metal on a plant design stage is used as a metal under evaluation, and
   wherein a replacement timing of the metal material is predicted on the basis of the predicted corrosion rate of crevice corrosion of the predicted corrosion rate of pitting of the metal.

5. The metal corrosion resistance evaluation method according to claim 4,
   wherein a corrosion rate of crevice corrosion or a corrosion rate of pitting of the metal under evaluation is predicted on the basis of a correlation between a maximum surface potential difference and corrosion rates in the liquid of two or more metals with different compositions, of which a corrosion rate of a crevice corrosion depth or a pitting depth in the liquid is known.

6. The metal corrosion resistance evaluation method according to claim 4,
   wherein the metal under evaluation is a stainless steel.

7. A metal material corrosion resistance evaluation device comprising:
   a potential measurement device for measuring surface potentials of a sample in a liquid, the potential measurement device including a probe, an alternating-current source for applying a bias voltage between the probe and a metal serving as the sample, a capacitor provided in a closed circuit for applying the bias voltage between the probe and the sample, a displacement measurement unit for outputting a voltage signal associated with an interacting force exerted between the probe and the sample, and a signal detector for detecting an electrostatic force signal having a specific frequency component contained in the voltage signal output by the displacement measurement unit to output a value corresponding to the detected signal;
   a database storing a relation between a surface potential difference in a microstructure of a metal with various compositions in a specific liquid, and a corrosion rate of a crevice corrosion or a pitting; and
   a prediction means for calculating a surface potential difference in the microstructure of the metal from the surface potentials measured by the potential measurement device, and for predicting a corrosion rate of a crevice corrosion or a corrosion rate of a pitting of the metal on the basis of the surface potential difference in the microstructure of the metal by referring to data in the database.

8. The metal material corrosion resistance evaluation device according to claim 7,
   wherein a frequency of an alternating-current voltage output by the alternating-current source is 10 kHz or more.

9. The metal material corrosion resistance evaluation device according to claim 8,
   wherein the alternating-current source includes:
   a first alternating-current source for applying a first alternating-current voltage between the electrode and the sample; and
   a second alternating-current source for applying a second alternating-current voltage in addition to the first alternating-current voltage between the electrode and the sample, the second alternating-current voltage having a frequency different from a frequency of the first alternating-current voltage.

10. The metal material composition prediction method according to claim 9, wherein a surface potential of a metal with various compositions in a specific liquid is measured in advance as a surface potential difference with respect to a reference metal, and compositions of a plurality of precipitates having sizes from 1 nanometer to 100 micrometers are predicted using the surface potential difference.

11. The metal material composition prediction method according to claim 9,
wherein an area ratio of a region having a specific precipitate potential with respect to a total area is determined through image processing on the basis of the surface potential distribution, and a content of a precipitate precipitated in a metal structure is predicted on the basis of the area ratio.

12. The metal material corrosion resistance evaluation device according to claim 7, further comprising:
scanners for X and Y directions for scanning the probe on a sample surface; and
a scanner for a Z direction for fitting the probe with unevenness of the sample,
wherein a movement amount of the scanners for the X and Y directions is 100 μm or more.

13. A metal material composition prediction method comprising:
measuring a surface potential of a metal under evaluation in a state in which the metal is immersed in a usage-environment liquid to determine a surface potential distribution of the metal;
calculating a surface potential difference in a microstructure of the metal on the basis of the surface potential distribution; and
predicting a composition of a precipitate precipitated in a metal structure on the basis of the calculated surface potential difference.

14. A metal material composition prediction device comprising:
a potential measurement device for measuring surface potentials of a sample in a liquid, the potential measurement device including a probe, an alternating-current source for applying a bias voltage between the probe and a metal serving as the sample, a capacitor provided in a closed circuit for applying the bias voltage between the probe and the sample, a displacement measurement unit for outputting a voltage signal associated with an interacting force exerted between the probe and the sample, and a signal detector for detecting an electrostatic force signal having a specific frequency component contained in the voltage signal output by the displacement measurement unit to output a value corresponding to the detected signal;
a database storing data on a surface potential difference between a surface potential of a metal with various compositions and a surface potential of a reference metal; and
a prediction means for calculating a surface potential difference in a microstructure of the metal from the surface potentials measured by the potential measurement device, and for predicting a composition of a precipitate precipitated in a metal structure on the basis of the surface potential difference measured by referring to data in the database.

* * * * *